(12) United States Patent
Lowenstein

(10) Patent No.: US 8,756,122 B2
(45) Date of Patent: Jun. 17, 2014

(54) INTELLIGENT REFRIGERATOR FOR STORING PHARMACEUTICAL PRODUCT CONTAINERS

(75) Inventor: Alan J. Lowenstein, New Providence, NJ (US)

(73) Assignee: Merck Sharp & Dohme Corp., Rahway, NJ (US)

(*) Notice: Subject to any disclaimer, the term of this patent is extended or adjusted under 35 U.S.C. 154(b) by 771 days.

(21) Appl. No.: 12/832,714

(22) Filed: Jul. 8, 2010

(65) Prior Publication Data

US 2010/0275625 A1 Nov. 4, 2010

Related U.S. Application Data

(63) Continuation of application No. 11/913,096, filed as application No. PCT/US2007/060524 on Jan. 12, 2007, now Pat. No. 7,775,056.

(60) Provisional application No. 60/759,738, filed on Jan. 18, 2006.

(51) Int. Cl.
  *G06Q 10/00* (2012.01)
(52) U.S. Cl.
  USPC ............ 705/28; 705/300; 62/60; 62/126; 62/127; 62/129; 62/157; 62/158; 62/231; 235/382; 235/375; 235/385
(58) Field of Classification Search
  USPC ........... 62/126, 127, 129, 60, 157, 158, 231; 235/385, 382, 375; 705/28, 300
  See application file for complete search history.

(56) References Cited

U.S. PATENT DOCUMENTS 6,170,746 B1 * 1/2001 Brook et al. ............... 235/385
(Continued)

*Primary Examiner* — Frantz Jules
*Assistant Examiner* — Azim Abdur Rahim
(74) *Attorney, Agent, or Firm* — Law Offices of Grady L. White, LLC

(57) ABSTRACT

Intelligent refrigerator system for storing pharmaceutical product containers, such as vials, ampules, syringes, bottles, medication tubes, blister packs and cartons, at the point of dispensing. Embodiments of the invention use product identification technology, such as radio-frequency identification (RFID) tags and readers, to uniquely identify containers as they are added to or removed from the cold storage compartment of the refrigerator, and automatically retrieve from a local or remote database a variety of details associated with the containers and their contents, such as manufacturing data, expiration dates, time out of refrigeration, inventory levels, safety information, usage statistics, known contraindications and warnings, etc. If the details indicate that there is a problem with a particular pharmaceutical (e.g., that it is counterfeit, expired, suspect, spoiled, recalled or almost depleted), then a message or warning is automatically delivered to a human operator via an attached output device, such as a display screen, speaker or printer. Embodiments of the invention may also be configured to monitor and report temperature faults, power failures and other anomalies associated with the refrigerator or cold storage compartment.

22 Claims, 11 Drawing Sheets

(56) References Cited

U.S. PATENT DOCUMENTS

| | | |
|---|---|---|
| 6,519,963 B2 | 2/2003 | Maeda |
| 6,892,545 B2 | 5/2005 | Ishikawa |
| 6,982,640 B2 | 1/2006 | Lindsay et al. |
| 7,178,729 B2 | 2/2007 | Shaffer et al. |
| 2002/0023441 A1* | 2/2002 | Bara et al. ......... 62/125 |
| 2004/0210419 A1* | 10/2004 | Wiebe et al. ......... 702/182 |
| 2004/0260470 A1 | 12/2004 | Rast |
| 2005/0088306 A1* | 4/2005 | Andreasson et al. ...... 340/573.1 |
| 2005/0091996 A1* | 5/2005 | Ishikawa et al. ......... 62/126 |
| 2005/0184153 A1 | 8/2005 | Auchinleck |
| 2005/0232747 A1 | 10/2005 | Brackmann et al. |
| 2005/0247782 A1* | 11/2005 | Ambartsoumian ......... 235/385 |
| 2006/0006999 A1 | 1/2006 | Walczyk et al. |
| 2006/0054682 A1* | 3/2006 | de la Huerga ......... 235/375 |
| 2008/0215461 A1 | 9/2008 | Bodin et al. |

* cited by examiner

FLOW 7 - TIMER CONT'D

INTELLIGENT REFRIGERATOR FOR STORING PHARMACEUTICAL PRODUCT CONTAINERS

CROSS-REFERENCE TO RELATED APPLICATIONS

This is a continuation application of U.S. application Ser. No. 11/913,096 (now U.S. Pat. No. 7,775,056, granted Aug. 17, 2010), filed on Oct. 30, 2007, which is a national stage entry under 35 USC 371(c) of International Application No. PCT/US2007/60524, filed on Jan. 12, 2007, which claims priority to U.S. provisional application No. 60/759,738, filed on Jan. 18, 2006, all of which are incorporated herein in their entirety by this reference.

FIELD OF THE INVENTION

The present invention relates generally to cold storage systems for pharmaceutical product containers.

BACKGROUND OF THE INVENTION

Refrigerated pharmaceutical products, such as vaccines, are very sensitive to rises in temperature and the passage of time. Professionals who dispense these products know that their quality, effectiveness and safety depends, to a very large extent, on the temperature conditions at the location where they are stored, the length of time they are stored at the location before being used, as well as the total amount of time the products have been outside of refrigeration since they were manufactured.

Generally speaking, refrigerated pharmaceutical products are also valuable and expensive, which attracts a large number of companies and individuals interested in marketing and distributing generic and counterfeit versions of high-demand pharmaceutical products for financial gain. Therefore, for health, safety and liability reasons, professionals who dispense branded pharmaceutical products must also be very concerned with maintaining the appropriate level of inventory on hand, acquiring additional products only from authorized sources, verifying the authenticity of the products received from authorized sources, and keeping track of the location or dispensing of every authorized product container.

Pharmaceutical product containers are usually marked with a product's name, manufacturer and expiration date. But these details are usually checked manually and only by visual inspection, which can lead to mistakes. These mistakes can have severe, long-lasting or permanent consequences. Moreover, the product's name, manufacturer and expiration date are only three of potentially dozens of very significant details associated with a particular pharmaceutical product container, which details the dispensing professional may need to take into account at the point of dispensing the product.

For instance, in addition to knowing the product's name and expiration date, a dispensing professional often needs or wants to know how long the particular product can stay outside of refrigeration without spoiling or losing its effectiveness. She may also want or need to know how long the product actually has been outside of refrigeration, either because the product was temporarily removed from the refrigerator or because the refrigerator in which it was kept temporarily lost power. She may also wish to know whether the pharmaceutical product has been recalled, whether it is authentic or counterfeit, whether the refrigerator where the product is kept is working properly, as well as a variety of other significant details too numerous to track manually.

Unfortunately, the conventional refrigerators for pharmaceutical product containers provide no way for physicians and other health care professionals to accurately and precisely ascertain these additional product details. Therefore, there is considerable need in the healthcare industry for a refrigerator for pharmaceutical product containers which provides a variety of pertinent details about the individual product containers that are inside the refrigerator, or that are being added or removed from the refrigerator, as well as a variety of significant details concerning the status and operation of the refrigerator itself.

SUMMARY OF INVENTION

The present invention addresses the above-described needs, as well as other shortcomings associated with the conventional pharmaceutical product refrigerators, by providing an intelligent refrigerator for storing pharmaceutical product containers, such as vials, ampules, syringes, bottles, jars, medication tubes, blister packs and cartons, which, among other things, uniquely identifies pharmaceutical product containers as they are added to or removed from the cold storage compartment, and reports to a human operator a variety of informative details and/or warnings associated with the uniquely-identified pharmaceutical product containers. Embodiments of the invention may also be configured to monitor and report to the human operator status anomalies associated with the cold storage compartment, and to perform certain functions necessitated by of the occurrence of such anomalies.

More specifically, embodiments of the invention automatically retrieve from a local or remote database a variety of details associated with the pharmaceutical product containers and their contents, such as manufacturing data, expiration dates, time out of refrigeration, inventory levels, safety information, usage statistics, and known contraindications and warnings. If the set of details indicates that there is a problem with a particular pharmaceutical (e.g., that it is counterfeit, expired, suspect, spoiled, recalled or almost depleted), then a message or warning may be automatically delivered to a human operator via an attached output device, such as a display screen, speaker or printer. Embodiments of the invention may also be configured to monitor and report temperature faults, power failures and other anomalies associated with the refrigerator or cold storage compartment. Embodiments of the invention may include one or more input devices, such as a touchpad, keyboard or mouse, which the human operator may use to provide operational instructions or print reports. Some embodiments also may be configured to automatically reorder pharmaceuticals when the product details indicate that a current inventory of any particular pharmaceutical has fallen below a specified level.

In general, embodiments of the invention comprise a cold storage compartment, a product identifier, a local database, an interface to a pharmaceutical product database, and one or more processors configured to monitor and manage certain events related to the pharmaceutical product containers. An event occurs, for example, when a pharmaceutical product container is added to or removed from the refrigerator's cold storage compartment, or when sensors indicate that there has been a power failure or an adverse temperature change.

The local database and the pharmaceutical product database are both configured to store a set of pertinent details associated with the pharmaceutical product container, such as the name of the vaccine, biologic, antitoxin or other compound it contains, the name of the manufacturer, the lot number, the date of manufacture, an expiration date, storage and refrigeration requirements, warnings, dosage, use instructions, etc. The pharmaceutical product database, which is typically pre-populated and provided by the manufacturer of the pharmaceutical, may reside on a remote computer system connected to an interconnected data communications network, such as the Internet or a corporate intranet, or on a permanent or removable memory storage area located within or attached to the refrigerator. If the pharmaceutical product database resides on a remote computer system attached to a data communications network, then the interface comprises a network interface to the data communications network. If the pharmaceutical product database resides in a local memory storage area, such as a CDROM or flash memory device, then the interface will typically comprise a bus and bus adaptor configured to provide a communications path between the memory storage area and one or more microprocessors executing the instructions provided by the one or more event monitoring and event managing processors.

The product identifier can be implemented using a variety of different product identification technologies, including but not limited to radio-frequency identification (RFID) tags and readers, barcode labels and readers and magnetic stripes and magnetic stripe readers. In some embodiments of the invention, for instance, an RFID reader and antenna are used to detect and decode a unique identifier (called a "tag") transmitted from a transponder embedded in the pharmaceutical product container. When the pharmaceutical product container with the transponder enters or leaves the antenna's read zone (i.e., its reception range), the RFID reader decodes the transponder signal produced by the pharmaceutical product container to determine the unique identifier associated with the container. Then the one or more event processors use the unique identifier to perform a variety of actions, such as determining whether the container has exceeded a time out of refrigeration limit, updating the location information for the container in the local database, sending an alert to the human operator of the refrigerator, and the like. Depending on the unique identifier received and the set of details associated with the unique identifier, the event processor may, in some cases, do nothing in response to the event (for example, if a duplicate read of the same container has occurred).

The event monitoring and event managing processor(s) may be embodied, for example, in one or more software application programs, routines or modules configured to be executed by a general purpose microprocessor, in one or more hardware devices, such as a programmable logic controller (PLC), in one or more firmware devices, or in some combination of software application programs, hardware and/or firmware devices. Typically, although not necessarily, the event monitoring processor (hereinafter referred to as the event monitor) is configured to monitor and detect new events associated with pharmaceutical product containers placed in or near the refrigerator, as well as to monitor and detect new events associated with the refrigerator itself. In some embodiments, the event monitor will generate event codes indicating what type of event has occurred. The event managing processor (hereinafter referred to as the event manager) typically carries out a series of instructions that are appropriate for the particular event that has just occurred. Notably, alternative embodiments of the invention may use fewer or more PLCs, computer software programs, modules or routines to perform the same functions as the event monitor and event manager. In some embodiments, for example, the functions of the event monitor and the event manager may be performed by the same hardware or software processor.

The product identifier and the event monitor will together determine the unique identifier for the container and what event has just occurred, such as whether the product container has been added or removed from the refrigerator. If event codes are used, then the event monitor will then generate an appropriate event code. The event manager receives the event code and the unique identifier from the event monitor and, depending on which event code was received, performs the appropriate action and/or transmits the appropriate message or warning to the human operator via an output device attached to the refrigerator.

For example, when a human operator places a pharmaceutical product container onto a shelf in the cold storage compartment, the container will necessarily pass into the read zone of an antenna located on, in or near the shelf. The antenna picks up a self-identifying signal transmitted from the transponder embedded in the container and sends the signal to the RFID reader. The RFID reader decodes the self-identifying signal to determine the unique identifier (tag) for the container and passes this information to the event monitor. The event monitor generates an "added item" event code signifying the fact that a product container has been added to the refrigerator (as opposed to being removed) and passes this information to the event manager, which then executes a series of checks and/or other actions associated with adding items to the refrigerator.

For instance, in response to receiving the added item event code, the event manager will first determine whether the local database already contains the unique identifier and a set of details (e.g., product name, expiration date, time out of refrigeration, etc.) associated with that unique identifier. If the unique identifier and set of details do not exist in the local database, then the event manager knows that this is the first time the container has been put into the refrigerator (i.e., it was not put in the refrigerator at some previous time and then temporarily removed). In this case, the event manager will access the pharmaceutical product database via the interface and search for the unique identifier. If the unique identifier is found in the pharmaceutical product database, then the event manager will copy the set of details associated with the unique identifier from the pharmaceutical product database to the local database via the interface.

If the unique identifier is not found in the local database or the pharmaceutical product database, or if the system cannot access the pharmaceutical database for any reason (such as a network connection being down), then the system will store a record in the local database indicating that there is a pharmaceutical product container in the cold storage compartment with a status that is unknown or suspect (i.e., not verified). Some embodiments of the invention will also send a message to this effect to an output device, such as a display screen, speaker or printer. Preferably, the event manager is also configured to periodically attempt to re-check the pharmaceutical product database to identify and/or verify containers that have been marked as unknown or suspect.

On the other hand, if the event manager determines that the local database already contains the unique identifier and a set of details associated with the unique identifier, then the system knows that the container was placed in the refrigerator previously and was temporarily removed. In this case, the event manager will record the current time the pharmaceutical product container was added to the refrigerator, calculate a time out of refrigeration value for the pharmaceutical product container based on the current time and a removal time value stored in the local database, and increment a counter or database item configured to track the total accumulated time out of refrigeration for the container.

One of the items in the set of details in the local database contains a maximum time out of refrigeration value for the pharmaceutical product container. Typically, this maximum time out of refrigeration value will be supplied by the manufacturer. If the total accumulated time out of refrigeration counter exceeds the specified maximum time out of refrigeration, then the event manager will transmit a warning message to the human operator, via the output device, indicating this fact. Preferably, the event manager is also configured to transmit instructions informing the human operator how to properly dispose of the product container.

If the human operator removes a pharmaceutical product container from the read zone of the antenna, the RFID reader will detect the removal and determine the unique identifier for the container removed. The event monitor will then generate and pass to the event manager a "removed item" event code. In response to receiving the removed item event code, the event manager looks up the unique identifier in the local database, records the time that the pharmaceutical product container with the unique identifier was removed from the read zone of the antenna, and sends a message to the output device containing pertinent details about the container just removed, such as the product name, the time of removal, dosing or usage instructions, authenticity status, etc.

In some embodiments of the invention, the cold storage compartment includes one or more temperature sensors that monitor the temperature in the vicinity of the pharmaceutical product containers stored therein. If the temperature rises above or falls below a specified level (e.g., rises or falls to a level that will negatively affect the quality and efficacy of the compound in one or more pharmaceutical product containers), then the event monitor will generate and pass to the event manager a temperature event code indicating that there is a temperature fault. In response to receiving the temperature event code, the event manager will transmit a message and/or warning concerning the temperature fault to the human operator via the output device. Such a message or warning may comprise, for example, warning beeps or a recorded voice message emanating from an attached speaker, a text message flashing on an attached display screen, or some combination of warning beeps, voice recordings and flashing text. Some embodiments also may be configured to send an email message concerning the fault to a human operator via the network interface.

As previously noted, the product identifier may be implemented using a variety of different product identification technologies. Some embodiments use one or more antennas located within the cold storage compartment, and a radio-frequency identification reader. The antenna is configured to convert a radio-frequency field produced by a transponder affixed to the pharmaceutical product container into alternating current, and the radio-frequency identification reader is configured to decode the alternating current to determine the unique identifier. In another embodiment, the product identifier comprises a barcode reader that determines the unique identifier by decoding a light energy signal reflected from a barcode label affixed to the pharmaceutical product container. In yet another embodiment, the product identifier comprises a magnetic stripe reader that detects changes in a magnetic field produced by a magnetic stripe affixed to the pharmaceutical product container. In this case, the changes in the magnetic field represent the unique identifier.

Some embodiments of the refrigerator also include one or more input devices (e.g., keyboard, keypad, mouse, touch screen, etc.) that can be activated by a human operator to provide operational instructions. Such operational instructions may include, for example, instructions to print certain reports, to change the temperature of the cold storage compartment, to revise or delete certain items from the local database, or to retry an attempt to connect to a particular manufacturer's pharmaceutical product database. The input devices may also include one or more biometric sensors (e.g., fingerprint or retina scanners) configured to verify the identity and authorization level of the human operator.

If the human operator strikes keys on the keyboard or touches the touch screen, for example, the event monitor will generate and pass to the event manager an "input" event code, which will cause the event manager to display a prompt and/or a menu on the display screen. The human operator can activate buttons on a keypad, keyboard, mouse or touch-sensitive display screen to specify what action she wishes to be performed. The event manager is configured to receive the human operator's instructions via the input device, execute the instructions, and then transmit an appropriate message or response to the operator via the output device.

In some embodiments of the invention, the event monitor is also coupled to a power fail circuit, which is configured to detect a power failure condition, such as a power outage. When this happens, the event monitor will generate and pass to the event manager a "power failure" event code, which causes the event manager to determine the starting time of the power outage, and then store the power failure event code and the starting time of the power outage in a status log. Preferably, the system is configured to accomplish these tasks on a high priority basis as soon as a drop in power is detected but before the power is depleted. Alternatively, the system may be configured to accomplish these tasks while the system is operating under the support of an emergency temporary power source, such as a battery or uninterruptible power supply (UPS). Such an emergency power source may also be used by the system to power an internal clock designed to keep track of the current time so long as the power failure condition persists.

When the regular power is restored, the event manager is configured to warn the human operator that there has been a power failure and also check the time out of refrigeration status of each pharmaceutical product container inside the refrigerator. In particular, the event manager will search the status log for the power failure event code. If the power failure event code is found in the status log, then the event manager will transmit the message concerning the power outage to an output device and then perform the following actions: (i) determine the duration of the power outage based on the current time and the recorded starting time of the power outage, (ii) cause the product identifier to read the signals produced by each pharmaceutical product container in the cold storage compartment to determine their unique identifiers, (iii) search the local database for the time out of refrigeration counters associated with each unique identifier, and (iv) if the sum of the duration and the time out of refrigeration counter for a unique identifier exceeds a specified maximum, then transmit a message concerning the unique identifier to an output device. In alternative embodiments, the event manager may be configured to simply update the time out of refrigeration counter in the local database for each pharmaceutical product container, and then check this counter at a later time as part of a periodic routine.

As will be discussed in more detail below, embodiments of the invention also may include one or more external product identifiers for detecting and reading unique identifiers transmitted from transponders affixed to pharmaceutical product containers located near the refrigerator but not actually placed inside the refrigerator's cold storage compartment. As will be discussed below, a human operator may use the external product identifiers, for example, to acquire details pertaining to individual pharmaceutical product containers without having to put those containers into the cold storage compartment. Such external product identifiers may also be configured to detect and decode the presence of other self-identifying items, such as transponder-embedded employee badges or access keys, which may be required to operate embodiments of the invention in secure environments.

BRIEF DESCRIPTION OF THE DRAWINGS

The present invention and various aspects, features and advantages thereof are explained in detail below with reference to exemplary and therefore non-limiting embodiments and with the aid of the drawings, which constitute a part of this specification and include depictions of the exemplary embodiments. In these drawings.

DETAILED DESCRIPTION OF EXEMPLARY EMBODIMENTS

With reference to the figures, a detailed discussion of exemplary embodiments of the invention will now be presented. Notably, the invention may be implemented using software, hardware, firmware, or any combination thereof, as would be apparent to those of skill in the art upon reading this disclosure.

Figure 1:
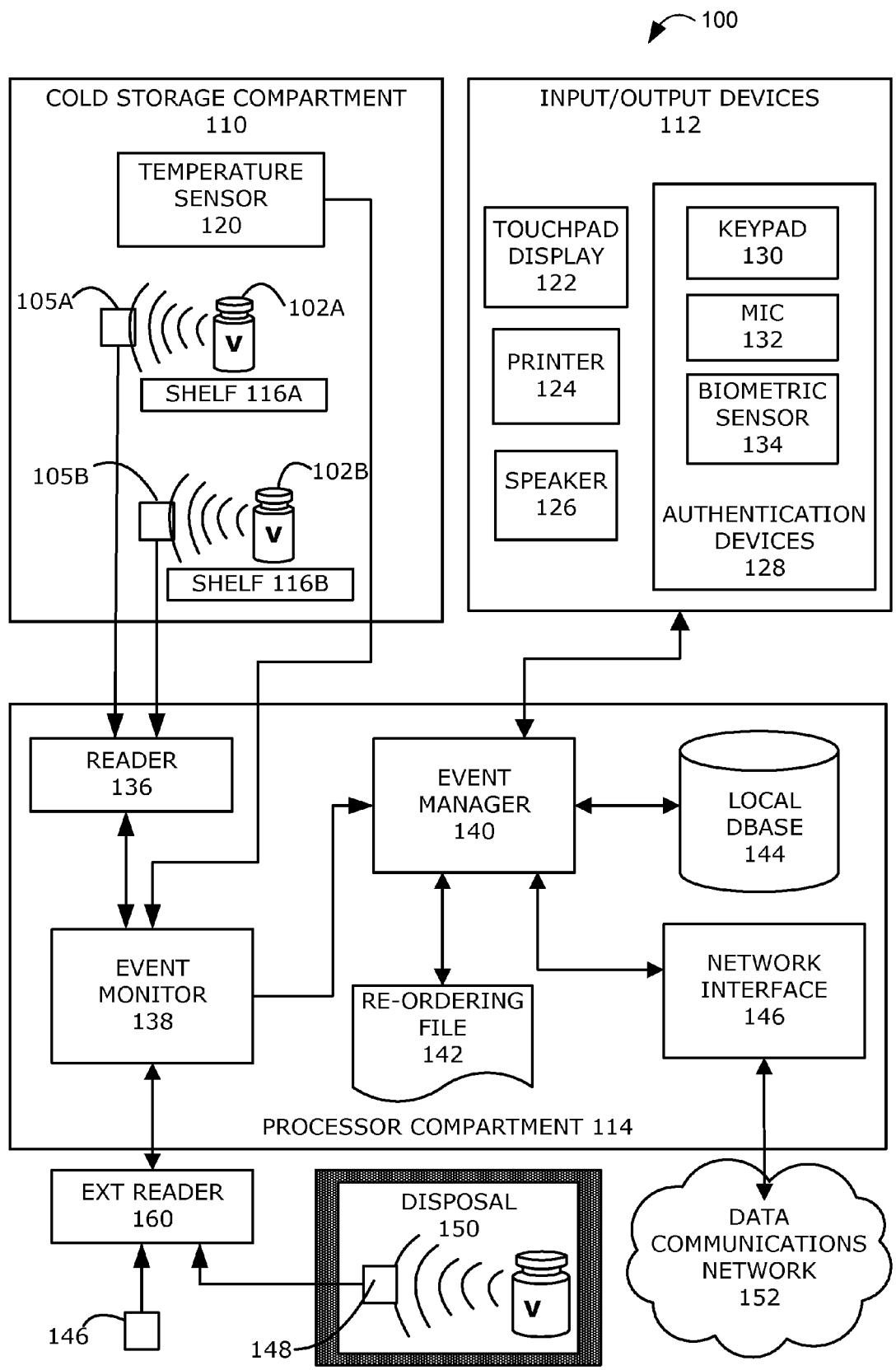
FIG. 1 contains a high-level block diagram illustrating the major functional components of a refrigerator configured to operate according to an embodiment of the invention.

FIG. 1 contains a high-level block diagram illustrating the major functional components of an embodiment of the invention. As shown in FIG. 1, refrigerator 100 generally comprises a cold storage compartment 110 (such as a refrigerator or freezer), a processor compartment 114 and input/output devices 112. Cold storage compartment 110 comprises one or more shelves or other supports (shown in FIG. 1 as shelves 116A and 116B) adapted to hold one or more pharmaceutical product containers (shown in FIG. 1 as vaccine vials 102A and 102B) embedded with transponders configured to transmit self-identifying signals. As previously noted, embodiments of the invention may be used to store a variety of other types of pharmaceutical product containers, including but not limited to ampules, syringes, bottles, medication tubes, blister packs and cartons. Positioned on, near or within the shelves are RFID antennas 105A and 105B, which are configured so that their radio-frequency reception ranges (or "read zones") encompass any tagged containers placed on shelves 116A and 116B. Consequently, when vials 102A and 102B are placed on shelves 116A and 116B, antennas 105A and 105B will detect the self-identifying radio frequency signals generated by the transponders attached to or embedded in vials 102A and 102B.

Cold storage compartment 110 also includes a temperature sensor 120 (such as a thermometer), which is positioned to monitor the temperature in the vicinity of shelves 116A and 116B and vials 102A and 102B. Although FIG. 1 illustrates only two shelf supports, two vaccine vials and one temperature sensor, it is noted that embodiments of the invention may utilize a multiplicity of shelves capable of holding a multiplicity of vaccine vials, as well as a multiplicity of temperature sensors. Some embodiments may even be configured to separately measure the temperatures adjacent to each shelf in the refrigerator. Cold storage compartments having interior supports, shelves and thermometers suitable for these purposes are supplied, for example, by GEM Scientific Refrigerator Company (www.gem-scientific.com), located in Philadelphia, Pa.

Processor compartment 114 comprises a reader 136, event monitor 138, event manager 140, local database 144, re-ordering file 142 and network interface 146. Reader 136 is an event-driven RFID reader, whose primary function is to collect, decode and pass on information transmitted to the antennas 105A and 105B by the transponders embedded in vials 102A and 102B. RFID readers and antennas suitable for these purposes may be obtained, for example, from Tagsys, USA (www.tagsysrfid.com), located in Doylestown, Pa.

Reader 136 typically passes the unique identifier encoded in the self-identifying signals detected by antennas 105A and 105B to event monitor 138. Event monitor 138 comprises a decision-making software program or programmable logic controller configured to react to the presence, absence, addition or removal of the self-identifying signals from the read zone of the antennas tied to the reader. Thus, in some embodiments of the present invention, event monitor 138 will generate an event-identifying code in response to the reader 136 detecting that a tagged pharmaceutical product container (such as vial 102A) is currently located inside or has been added to or removed from cold storage compartment 110. Temperature sensor 120 is also tied to event monitor 138 so that event monitor 138 can also generate a temperature change-related event code in response to temperature changes in cold storage compartment 110.

While event monitor 138 determines what kind of event has occurred, event manager 140 selects the course of action to take and carries out the selected course of action. It is event manager 140, for instance, which checks and updates local database 144 whenever a pharmaceutical product container is added to or removed from cold storage compartment 110. When the local database 144 does not contain details associated with the unique identifier acquired from the pharmaceutical product container, then event manager 140 utilizes network interface 146 to gain access to a remote pharmaceutical product database (not shown in FIG. 1) via data communications network 152. Although FIG. 1 shows event monitor 138 and event manager 140 as two distinct components, those skilled in the computer arts will recognize that a single hardware, software or firmware component, or alternatively, a multiplicity of distinct hardware, software and firmware components may be utilized to implement the functions performed by event monitor 138 and event manager 140, as described herein, without departing from the spirit or the scope of the present invention.

Network interface 146 comprises wired and/or wireless network adapter cards, adapter card drivers, network cables, application programming interfaces, or modems and routers, as well as other networking software and hardware, typically used to connect a personal computer to an online data communications network. The online data communications network, such as data communications network 152 in FIG. 1, may comprise, for example, a local area network (LAN), a wide area network (WAN), a dedicated WAN, a corporate intranet, a virtual private network, or the Internet. Data communications network 152 may also include other pharmaceutical product refrigerators, similar to refrigerator 100, which allows users to set up and manage a network of pharmaceutical product container refrigerators operating according to the present invention.

As shown in the box labeled input/output devices 112 in FIG. 1, embodiments of the invention also may include one or more attached output devices, which event manager 140 uses to transmit messages and/or warnings to a human operator, as well as one or more attached input devices, which the human operator can activate to supply commands and instructions to the refrigerator. In particular, messages and warnings generated by event manager 140 can be displayed on touchpad display 122, printed on printer 124 and/or announced on speaker 126. Alternatively, embodiments of the invention can be configured to store information, error messages and warning messages in a local or remote log file (not shown in FIG. 1), which may be accessed by a human operator via the one or more attached input devices or distributed to human operators via e-mail, web page servers or online information publication services accessible through network interface 146 and data communications link 152. Printer 124, operating under the control of event manager 140, can also print status, inventory, product usage and new information reports, as well as self-adhesive customized pharmaceutical product labels and customized dosing instructions that can be affixed to the pharmaceutical product containers as they are placed into or removed from cold storage compartment 110. The input devices may include a keyboard or mouse (neither of which are shown in FIG. 1), a keypad 130, a microphone 132, a biometric sensor 134 (such as a retina or fingerprint scanner), or some combination of two or more of these devices. As indicated by the box in FIG. 1 labeled authentication devices 128, keypad 130, microphone 132 and biometric sensor 134 also may be configured to receive and verify security and authorization data, such as user identifications and passwords. The system may also be configured, for example, to receive security and authorization data through touch-operated menus displayed on the touch-pad display 122.

As will be described in more detail below, some embodiments of the invention may be configured to notify operators when particular pharmaceutical product inventories fall below certain levels and optionally prompt the human operator to provide an authorization for the system to create and submit a new order to a pharmaceutical manufacturer via network interface 146 and data communications network 152. Therefore, some embodiments of the invention may include a user-configurable re-ordering file 142, which stores a set of user preferences associated with certain pharmaceutical products. Event manager 140 can utilize the data in re-ordering file 142 to automatically create and submit orders. Alternatively, the re-ordering information for pharmaceutical products can be stored in the local database along with the other details and attributes of those pharmaceutical products. In the case of a data communications network (such as a corporate LAN) comprising multiple pharmaceutical product refrigerators, inventory and re-ordering information for the multiple refrigerators may be consolidated and stored in a centralized database so that purchasing decisions and new orders can be based on the consolidated inventory information for all of the refrigerators in a company or organization, rather than just a single refrigerator in the network. Preferably, the human operator can create and edit the re-ordering file 142 by using a keyboard, a mouse, or both (not shown in FIG. 1), or by activating and using touch-enabled menu screens displayed on touchpad display 122.

The embodiment of the invention shown in FIG. 1 also includes an external reader 160, external antennas 146 and 148, and disposal 150. External reader 160 and antenna 146 will detect and read self-identifying signals produced by transponders attached to pharmaceutical product containers that are located outside of cold storage compartment 110, but which are still within the read zone of antenna 146. External reader 160 and external antenna 146 are provided so that a human operator can easily obtain pertinent details concerning individual product containers without putting those individual product containers into cold storage compartment 110.

Suppose, for example, that the refrigerator is configured so that pharmaceutical product containers are stored inside cold storage compartment 110 in trays, and that each tray is capable of holding a large number of pharmaceutical product containers (say, twenty or thirty individual containers per tray). Suppose further that a human operator removes an entire tray from cold storage compartment 110, which causes the internal antennas 105A and 105B, reader 136, event monitor 138 and event manager 140 to cooperate to produce a warning message on touchpad display 122, printer 124, speaker 126, or all of them. The warning message indicates that, according to the details stored in local database 144, one or more of the pharmaceutical product containers in the removed tray should be destroyed or returned because it has expired or been recalled by the manufacturer.

At this point, however, the human operator may be holding a tray containing perhaps twenty or thirty containers. Therefore, it may not be immediately obvious, depending on the warning message and/or the number of containers in the tray, which containers are bad. One method the human operator can use to determine which containers are bad is to remove individual containers from the tray and return each of them to cold storage compartment 110 one at a time, keeping track of the individual containers that trigger additional warning messages. It is far safer, as well as far less cumbersome and time-consuming, however, for the human operator to separately move each of the individual containers into the read zone of the external antenna 146, so that external reader 160 (which, like reader 136, is also coupled to event monitor 138 and event manager 140) can determine and indicate via subsequent status and warning messages which containers are bad. Thus, there will be no need to put expired and/or recalled pharmaceutical product containers back into cold storage compartment 110.

Preferably, the human operator can place the bad pharmaceutical product containers in an attached receptacle for disposal (disposal 150 in FIG. 1) having another antenna (antenna 148 in FIG. 1), which is also attached to external reader 160 (as shown in FIG. 1) or alternatively, attached to reader 136. When antenna 148 detects a self-identifying signal produced by a pharmaceutical product container placed in disposal 150, event monitor 138 is configured to generate a "discarded product" event code indicating that the identified pharmaceutical product container has been discarded by the human operator. Upon receiving the discarded product event code, event manager 140 is configured to update the local database to reflect this fact, and print, display or announce an appropriate message for the human operator via one or more of the output devices.

Disposal 150 can also be used to discard empty pharmaceutical product containers—that is, containers for pharmaceutical products that have already been dispensed. The fact that the product has already been dispensed could then be stored in the local database by event manager 140 and, optionally, uploaded to the manufacturer's pharmaceutical product database. Thereafter, if a pharmaceutical product container having the same unique identifier appears in this or another refrigerator, users and manufacturers could be warned that the container may in fact be counterfeit. The event manager 140 may also be configured to ask the user, via touchpad display 122, for example, whether the discarded pharmaceutical product should be automatically re-ordered based on data stored in re-ordering file 142.

Although not shown in FIG. 1, embodiments of the present invention also include an emergency power supply, such as a battery and/or uninterruptible power supply (UPS), which will be activated in case of a power failure, thereby reducing the risk that a significant number of pharmaceutical product containers would have to be discarded due to a loss of power, and also providing the system with sufficient power during a power failure to carry out a predetermined power failure routine.

Embodiments of the present invention may be practically applied in a variety of different settings where refrigerated pharmaceutical products are usually stored, dispensed and/or administered, including for example, physicians' offices, hospitals and pharmacies. But the invention may also provide significant advantages outside of the usual settings, such as in homes and mobile clinics, which increasingly have constant high-speed wired and wireless connections to data communications networks, such as the Internet. Diabetes patients, for instance, frequently need to store insulin in home refrigeration units for significant periods of time. Physicians combating the spread of viruses and disease in the field often have to work out of mobile clinics, such as vans, that house, among other things, refrigeration units containing refrigerated vaccines. In these situations, embodiments of the present invention may be used (either as stand-alone units, or alternatively, as part of an upgrade kit for a conventional refrigerator) to provide potentially critical details about the authenticity, quality and status of pharmaceutical products at the time and place where they will be used.

Figure 2:
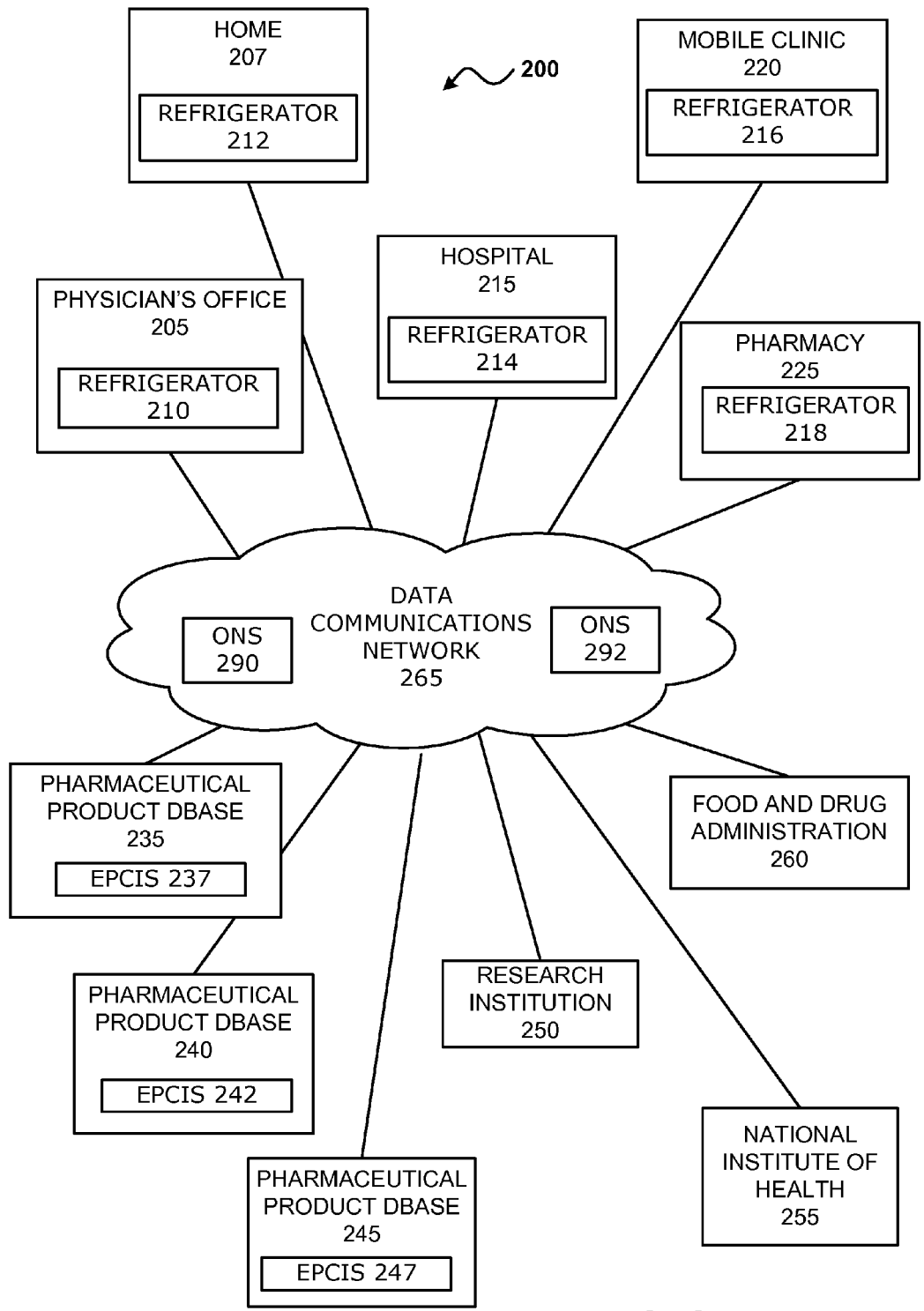
FIG. 2 contains an exemplary network in which embodiments of the invention may be used.

FIG. 2 illustrates, by way of example, a networked environment in which embodiments of the present invention may be beneficially implemented. As shown in FIG. 2, network 200 comprises a multiplicity of intelligent refrigerator users (shown in FIG. 2 as physician's office 205, home 207, hospital 215, mobile clinic 220 and pharmacy 225), which utilize a multiplicity of refrigerators 210, 212, 214, 216 and 218, respectively, to store pharmaceutical product containers. Refrigerators 210, 212, 214, 216 and 218 are configured to operate substantially in the same manner as refrigerator 100 described above with reference to FIG. 1. Thus, refrigerators 210, 212, 214, 216 and 218 each contain network interfaces, which enable refrigerators 210, 212, 214, 216 and 218 to connect, via data communications network 265, to a multiplicity of pharmaceutical product databases 235, 240 and 245. The pharmaceutical product databases are typically operated by the manufacturers of the pharmaceutical product containers.

To facilitate the communication and download functions between refrigerators 210, 212, 214, 216 and 218, on the one hand, and pharmaceutical product databases, on the other, data communications network 265 comprises one or more object naming servers (shown in FIG. 2 as ONS 290 and ONS 292), which provide object naming services ("ONS") for RFID tags. Similar to the role played by directory naming service (DNS), which provides root directory naming services on the Internet, ONS servers store and provide directory information for registered electronic product codes (EPCs) assigned to individual objects that carry RFID transponders. Each EPC is a unique identification number (like a serial number) that enables manufacturers, retailers, wholesalers and end-users to track goods as they move through their inventories and throughout the world. Pharmaceutical manufacturers register their EPCs with ONS server operators, who program the ONS servers to provide Internet protocol addresses for the manufacturers' online pharmaceutical product databases. The online pharmaceutical product databases supply pharmaceutical product container details to client computer systems according to an industry standard known as the EPC information service (EPCIS). Currently, Verisign, Inc. (www.verisign.com), of Mountain View, Calif., manages and operates Internet-based ONS servers for use by the public, in conjunction with EPCglobal, Inc. (www.epcglobaling.org), a not-for-profit consortium of RFID industry leaders, which provides industry-driven standards and designs for a rapidly-expanding Internet-based EPCIS network. Thus, as shown in FIG. 2, each one of the pharmaceutical product databases 235, 240 and 245 comprises an EPCIS-enabled server (shown in FIG. 2 as EPCIS 237, EPCIS 242 and EPCIS 247), which provides access to details contained in that pharmaceutical product database.

When a refrigerator of the present invention (such as refrigerator 210) connects to the data communications network 265 and supplies an ONS server (such as ONS 290 or ONS 292) with a registered unique identifier (EPC) embedded in a transponder attached to a pharmaceutical product container, the ONS server responds by providing the refrigerator with the Internet protocol address for an EPCIS-enabled pharmaceutical product database. Having obtained the appropriate Internet protocol address from the ONS server, the refrigerator can then connect (again, via data communications network 265) to the manufacturer's EPCIS-enabled pharmaceutical product database and retrieve details associated with the unique identifier (and, hence, the particular container). Where information security is a concern, the information transmitted between the refrigerator 210 and the manufacturer's EPCIS-enabled pharmaceutical product database via the data communications network may be encrypted.

By utilizing ONS and EPCIS, embodiments of the present invention may be configured to provide critical information concerning the distribution and status of refrigerated pharmaceutical product containers to other institutions which have an interest in tracking this kind of information. For instance, institutions such as medical research firms and universities, the National Institute of Health (NIH) and the Food and Drug Administration (FDA) (which are represented in FIG. 2 as research institution 250, National Institute of Health 255, and Food and Drug Administration 260) can also be connected to a multiplicity of intelligent pharmaceutical product refrigerators via data communications network 265. Therefore, if there were a sudden outbreak of a particular virus or disease, the National Institute of Health or the Centers for Disease Control (CDC), for instance, could rapidly determine through the invention and the data communications network the quantity and locations where the necessary vaccines are stockpiled and/or stored. On the other hand, the FDA, which, among other things, monitors newly discovered adverse events associated with drugs and vaccines, also may need to determine rather quickly where such drugs and vaccines are currently located throughout the country. Embodiments of the present invention make it possible for these organizations to quickly collect this kind of detailed information.

FIGS. 3 through 10 contain high-level flow diagrams illustrating the steps performed by a refrigerator configured to operate according to embodiments of the invention. These steps would be performed, for example, by event monitor 138, event manager 140, or both of them, as described above with reference to FIG. 1.

Figure 3:
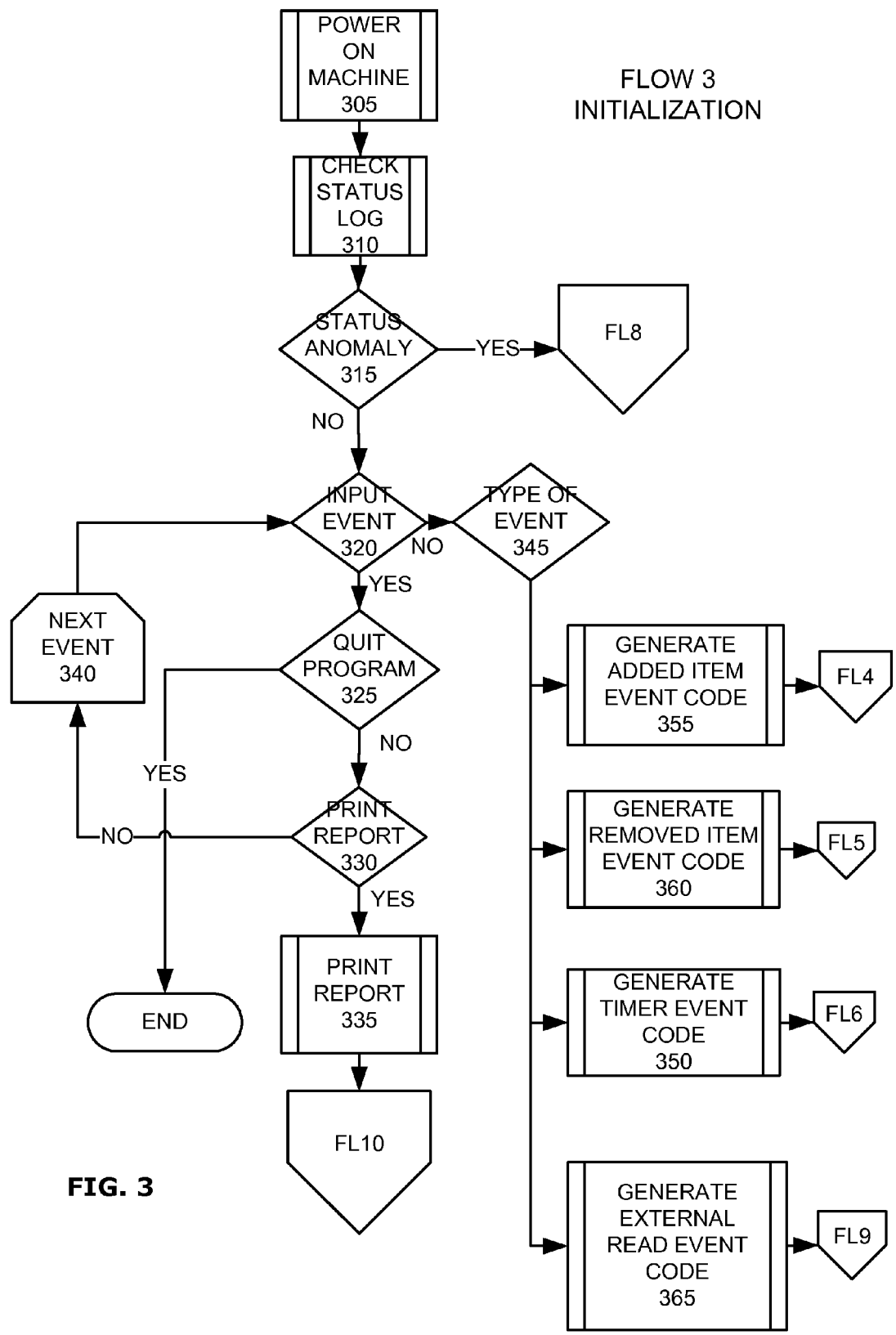
FIGS. 3 through 10 contain high-level flow diagrams illustrating the steps performed by a refrigerator configured to operate according to embodiments of the invention.

FIG. 3 illustrates the initialization procedures for embodiments of the invention. When the system is first powered on at step 305 of FIG. 3, event manager 140 checks the status log to determine, for example, whether there has been a status anomaly (see steps 310 and 315). A status anomaly may include, for instance, a power outage, a door being left open, the refrigerator being completely full, or any other problem or malfunction pertaining to the refrigerator itself, as opposed status problems pertaining to the pharmaceutical products containers inside the refrigerator. If a status anomaly has occurred, then processing continues at step 805 of FIG. 8 by way of flow chart connector "FL8." The anomaly procedures are discussed in more detail below with reference to FIG. 8. If it is determined at step 315 that no status anomaly has occurred, then the system determines, at step 320, whether the operator has caused an input event by, for example, striking keys on the keypad or activating the touchpad display. If an input event has occurred, the system checks whether the input event comprises a request to quit the program (step 325). If the answer is yes, then the program (e.g., event manager 140) terminates. But if the input event was not a request to terminate, then processing continues at step 330, where the system determines whether the operator has requested a printed report. If the answer is yes, then the system enters the print report procedures (step 335) and processing continues at step 1005 of FIG. 10 by way of flow chart connector "FL10." The print report procedures are discussed below with reference to FIG. 10. If it is determined at step 330 that the operator did not request a printed report, then the system loops back to step 320 to check for the next event by way of step 340.

If it is determined at step 320 that an event other than an input event occurred, then the system next determines, at step 345, which type of event occurred. Embodiments of the invention are configured to determine when pharmaceutical product containers are added or removed from the cold storage compartment, as well as when one of the external antennas has picked up a signal from a pharmaceutical product container located outside of the cold storage compartment. Thus, if it is determined at step 345 that a pharmaceutical product container has been added to the cold storage compartment, then an "added item" event code is generated (step 355) and processing will continue at step 405 of FIG. 4 by way of flow chart connector "FL4." If it is determined at step 345 that a pharmaceutical product container was removed from the cold storage compartment, then a "removed item" event code is generated (step 360) and processing continues at step 505 of FIG. 5 by way of flow chart connector "FL5."

Some embodiments of the invention are configured to determine on a periodic basis whether certain problems have occurred, such as a temperature or database detail problem. These are referred to as "timer events." Therefore, if it is determined at step 345 that a timer event has occurred, then a timer event code is generated (step 350) and processing will continue at step 605 of FIG. 6 by way of flow chart connector "FL6." And finally, if it is determined at step 345 that a pharmaceutical product container was brought within the read zone of an external antenna, then an "external read" event code will be generated (step 365) and processing will continue at step 905 of FIG. 9 by way of flow chart connector "FL9." The added item, removed item, timer event and external read event procedures are discussed in detail below with reference to FIGS. 4, 5, 6, 7 and 9.

Figure 4:
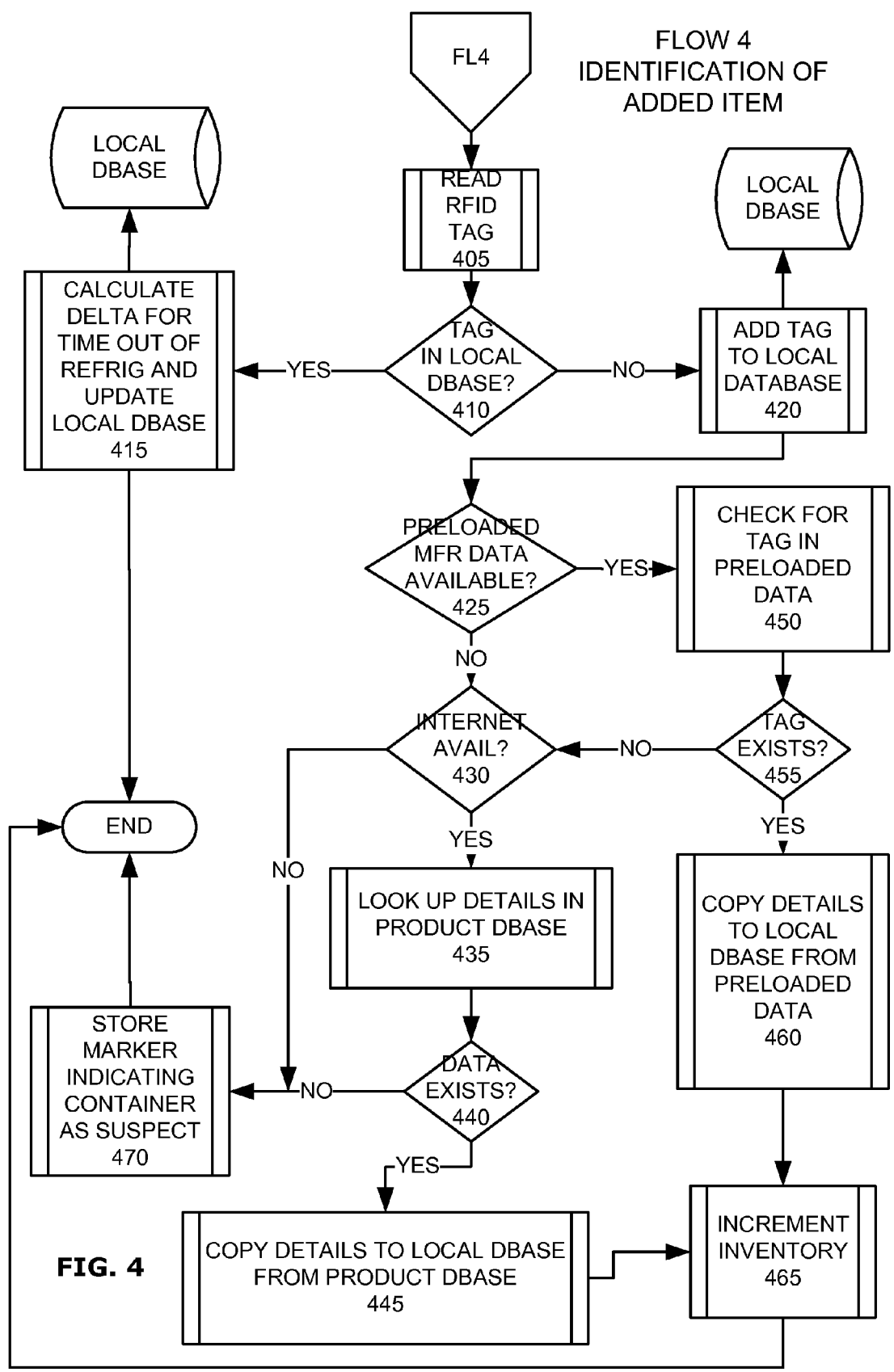

FIG. 4 contains a flow diagram illustrating the identification procedures certain embodiments of the invention will execute if an added item event occurs (i.e., if a pharmaceutical product container has been added to the cold storage compartment). As shown in FIG. 4, the first step (step 405) is to read the tag (i.e., the unique identifier or EPC) transmitted by the transponder attached to the pharmaceutical product container. At step 410, the system determines whether the tag already exists in the local database. If the tag already exists in the local database, then the pharmaceutical product container must have already been in the cold storage compartment at some point in the past, but was temporarily removed. Therefore, the next step (step 415 in FIG. 4) is to calculate the change in the total amount of time the pharmaceutical product container has been out of the cold storage compartment (i.e., the delta for the container's total time out of refrigeration) and update an appropriate counter in the local database. One way to perform this calculation is to maintain in the set of details associated with the pharmaceutical container a detail indicating the time the container was removed from the cold storage compartment (as done in step 530 of FIG. 5, which is discussed below). Then, when the container is added to the cold storage compartment, the time of removal detail is retrieved from the local database and compared to the current time. The current time may be obtained, for example, from an internal clock, or alternatively, from an Internet- or network-accessible clock. The difference between the current time and the time of removal equals the delta in the time out of refrigeration for the container. The delta is then added to a prior total time out of refrigeration value (also retrieved from the set of details in the local database) to obtain an updated total time out of refrigeration for the container. The updated total time out of refrigeration is then stored in the local database.

In some embodiments, the system will at this point compare the updated total time out of refrigeration to a specified maximum time out of refrigeration for the container and, if appropriate, transmit a warning message to the operator. In other embodiments, the procedure for comparing the updated total time out of refrigeration to the specified maximum will be performed as part of the timer event processing (see steps 765, 770 and 775 of FIG. 7, discussed below).

If it is determined at step 410 that the tag does not already exist in the local database, then the container has probably never been inside the cold storage compartment. Therefore, the system adds the new tag to the local database (step 420) and checks whether the system has access to preloaded manufacturer data residing in another memory storage location attached to the system, such as on a permanent or removable disk drive, CDROM, tape device or flash memory device (step 425). If the preloaded manufacturer data is not available, then the system determines whether the Internet (or another data communications network) is available (step 430). If the Internet is also not available, then the system will store in the local database a marker indicating that the container associated with the new tag is suspect (step 470) and the added item processing then comes to an end.

But if the Internet is available, then at step 435 the system will look up the details for the tag (and the container) in a remote pharmaceutical product database (using ONS and EPCIS, for example). If the tag and the details exist in the remote pharmaceutical product database (step 440), then the system copies the details from the remote pharmaceutical product database to the local database (step 445), increments any inventory counters in the local database (step 465) and terminates processing. If the tag and details are not found in the remote pharmaceutical product database, however, then the system stores in the local database a marker indicating that the container associated with the new tag is suspect (step 470) and terminates processing. As will be discussed below and with reference to FIG. 7, the system is preferably configured to automatically retrieve the suspect markers and attempt to verify and/or authenticate the suspect product containers at a later time when, for example, access to the Internet (or other data communications network) or pharmaceutical product database has been reestablished, or when the pharmaceutical product database may have been updated to include information concerning the suspect containers.

If it is determined at step 425 that preloaded manufacturer data is available, then the system searches the preloaded manufacturer data for the tag (step 450). If the tag and associated details are found in the preloaded manufacturer data, then the details associated with the new tag are copied from the preloaded manufacturer data to the local database (step 460), the inventory counters are incremented (step 465) and processing comes to an end. But if the tag and details are not found in the preloaded manufacturer data, then processing will continue at step 430, where the system looks for the tag and data on the Internet (as described above).

Figure 5:
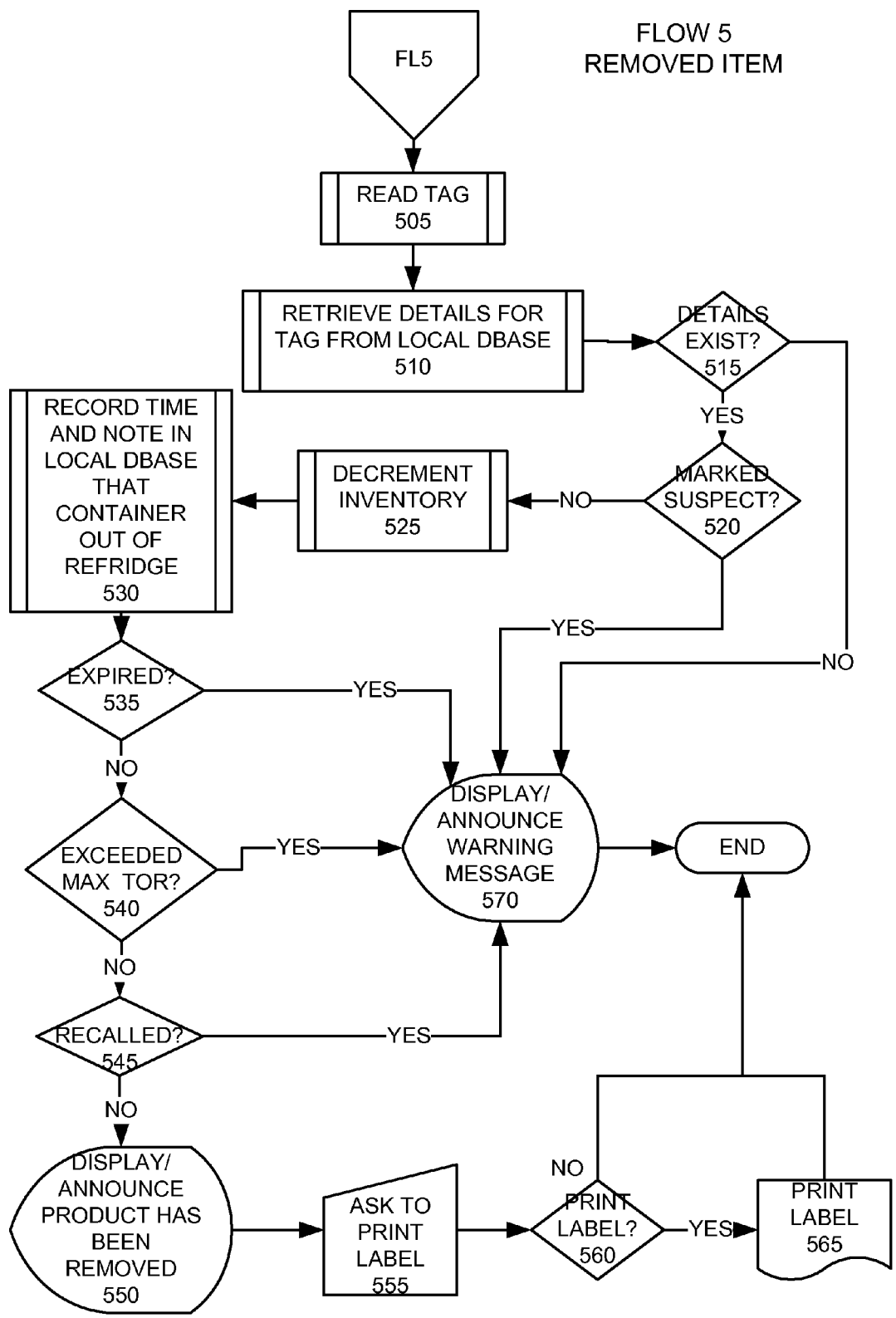

FIG. 5 contains a high-level flow diagram illustrating the steps performed by embodiments of the invention when a pharmaceutical product container is removed from the cold storage compartment. As shown in FIG. 5, the first steps are to read the tag for the removed item (step 505) and attempt to retrieve the details for the tag from the local database (steps 510 and 515). If the details for the removed container do not exist in the local database, then the system has no record of a container being stored in the cold storage compartment. Therefore, the system displays, prints and/or announces a suitable warning (step 570) to inform the operator. However, if there are details in the local database for the tag, then the system determines whether the tag has been marked as suspect (step 520). If the answer is yes, then again processing will proceed at step 570, where the system will display, print and/or announce a suitable warning or error message for the operator.

If the details for the tag exist in the local database and have not been marked as suspect, then the system decrements any inventory counters for the pharmaceutical product (step 525), and, at step 530, records the time the container was removed from the cold storage compartment and notes in the local database that the container has been removed. Some embodiments will also determine at this time whether the removed container has expired (step 535), exceeded its maximum time out of refrigeration (step 540) or been recalled (step 545). If any of these conditions are true, then the system again displays, prints and/or announces an appropriate error message or warning for the operator (step 570). But if none of these conditions are true, then the system displays, prints and/or announces that the container has been removed (step 550), and prints a label for the container if instructed to do so by the operator (steps 555, 560 and 565).

Figure 6:
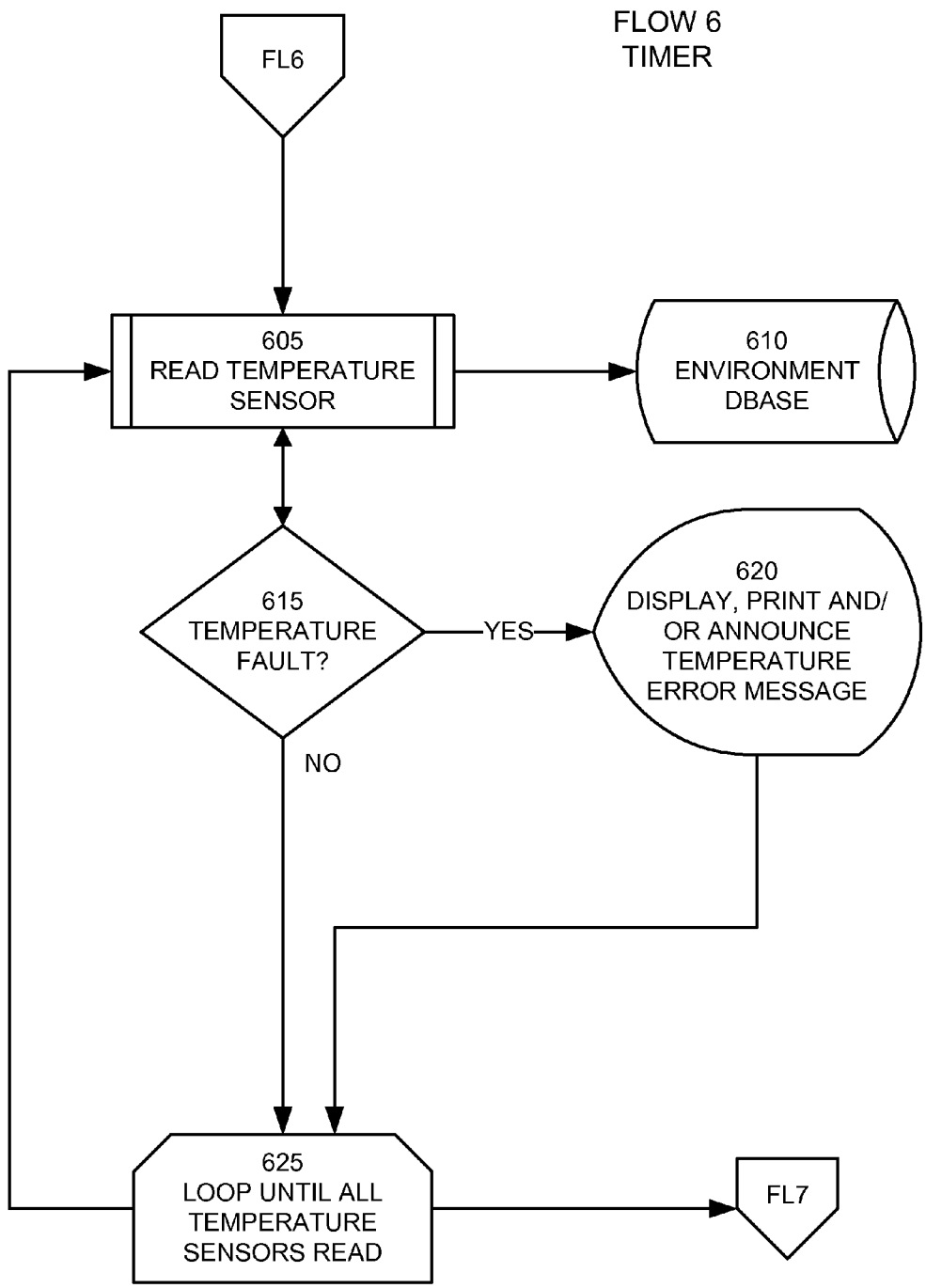
Figure 7:
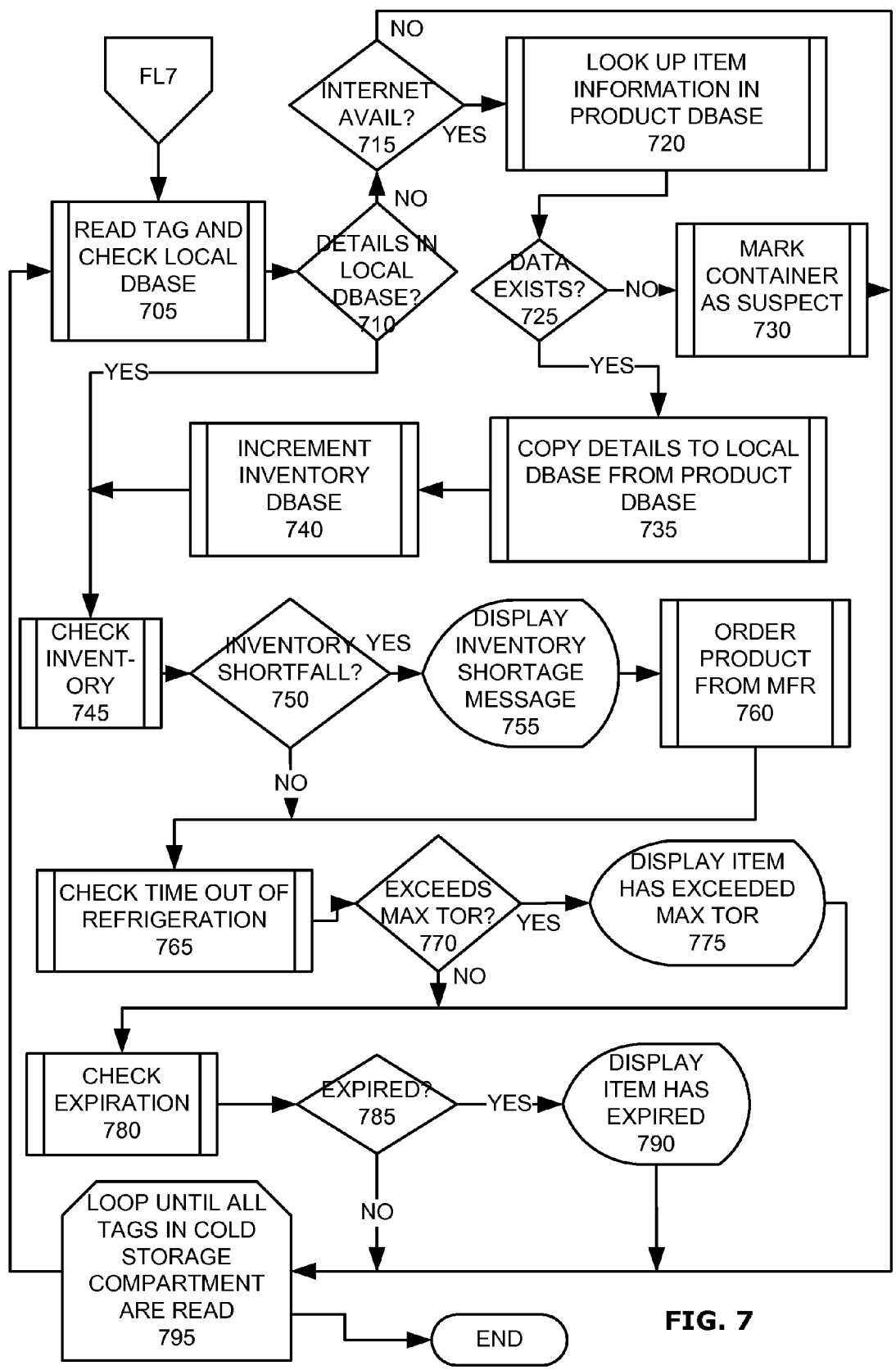

FIGS. 6 and 7 contain a high-level flow diagram illustrating the steps performed by embodiments of the invention when a timer event occurs. As shown in FIG. 6, the first steps are to read a temperature sensor in the cold storage compartment and compare the reading to data stored in an environment database to determine if a temperature fault has occurred (steps 605, 610 and 615). If a temperature fault has occurred, then the system will display, print or announce an appropriate error message (step 620). If the reading indicates that no temperature fault has occurred, then the system will continue looping through steps 605, 615 and 625 until all temperature sensors have been read. When all of the temperature sensors have been read, processing will continue at step 705 of FIG. 7 by way of flow chart connector "FL7."

At steps 705 and 710 of FIG. 7, the system reads a tag for a pharmaceutical product container located inside the cold storage compartment and then determines (at steps 710, 715, 720 and 725) whether the data can be found in the local database or in a product database located on the Internet. If the details for the tag are found only in the pharmaceutical product database and not in the local database, then the system will copy the details from the pharmaceutical product database to the local database (step 735) and increment the appropriate inventory counters (step 740). But if the details for the tag are not found in either database, then the system marks the container as suspect (step 730) and loops back to step 705 to begin processing the next tag. The system is configured to continue looping in this manner until all of the tags inside the cold storage compartment have been read (see step 795).

Once the details have been copied into the local database, the system next determines whether there is an inventory shortfall for the tag (steps 745 and 750). If so, the system displays an inventory shortfall message (step 755). In some embodiments, the system automatically orders additional products from the manufacturer (step 760). In other embodiments, the system prompts the user to order additional products by manual methods or sends an inventory shortfall notification message to a centralized inventory database so that re-ordering and purchasing decisions can be made using the inventory data from multiple refrigerators. Next, the system determines, at steps 765 and 770, whether the total time out of refrigeration for the tag exceeds a specified maximum. If so, then the system displays a message to the operator indicating this fact (step 775). Next, the system determines whether the product has expired (steps 780 and 785) and, if so, displays an appropriate message to that effect (step 790). All of these checks are determined for each container in the cold storage compartment (see step 795). When all of the containers and all of the temperature sensors have been checked, timer event code processing comes to an end.

Figure 8:
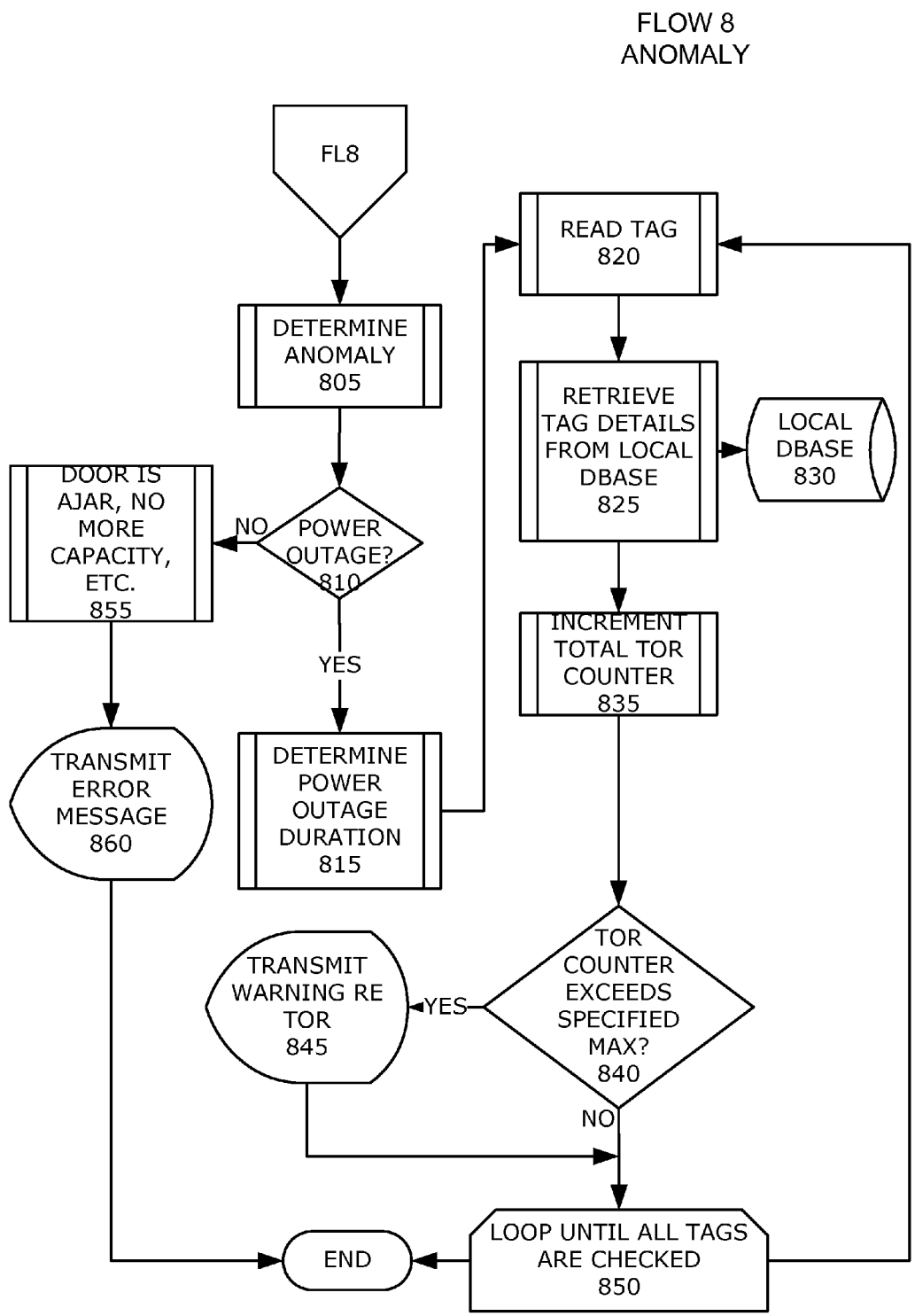

FIG. 8 contains a high-level flow diagram illustrating the steps performed by embodiments of the invention when an anomaly event code is generated. As shown in FIG. 8, the system first determines, at steps 805 and 810, whether a power outage has occurred. If not, the system may be configured to determine whether some other type of anomaly has occurred, such as a door being open, the refrigerator being at full capacity, a malfunction of an antenna, thermometer, printer, biometric sensor, or some other physical or functional problem (step 855), in which case the system will transmit the appropriate error message to an output device (step 860) and terminate processing. However, if it is determined at step 810 that a power outage has occurred, then the system determines the duration of the power outage (step 815), reads a tag on a container located in the cold storage compartment (step 820), retrieves the details for the tag from the local database (steps 825 and 830), and updates the total time out of refrigeration (TOR) counter for the tag (step 835). Next, the system compares the total time out of refrigeration (TOR) counter to a specified maximum time out of refrigeration (step 840). If the total time out of refrigeration (TOR) exceeds the specified maximum, then the system transmits an appropriate warning message to the operator via an output device (step 845). The system will then loop back to step 820 to begin processing the next tag for the next container in the cold storage compartment (see step 850). When all of the containers in the cold storage compartment have been processed, the anomaly event code processing comes to an end.

Figure 9:
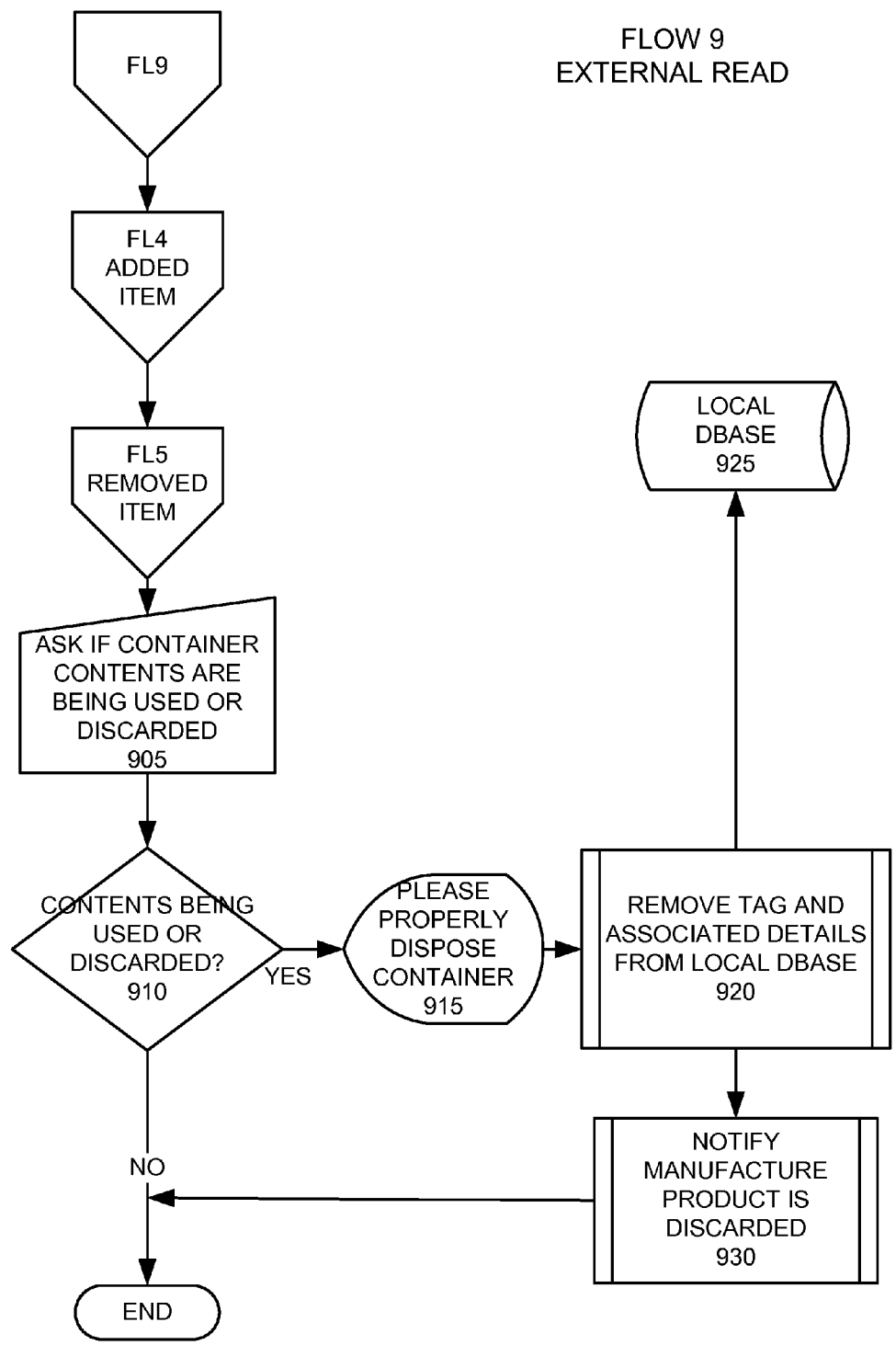

FIG. 9 contains a high-level flow diagram illustrating the steps performed by embodiments of the invention when an external read event code is generated. As shown in FIG. 9, the system first performs the same steps illustrated in FIGS. 4 and 5 and which were discussed above with reference to the added item and removed item event codes. Next, at step 905, the system asks the operator whether the product container contents are being used or discarded. If the answer is yes, then the system prints a message advising the operator to properly dispose of the container (step 915), removes the tag and associated details from the local database (step 920) and optionally sends a message to the manufacturer, via the network interface, that the container has been discarded (step 930). Supplied with the discarded container information, it will be easier for the manufacturer (or other interested parties) to identify as counterfeit containers having the same tag. The system may also be configured to prompt the user for permission to update a re-ordering file so that the used or disposed product may be automatically re-ordered.

Figure 10:
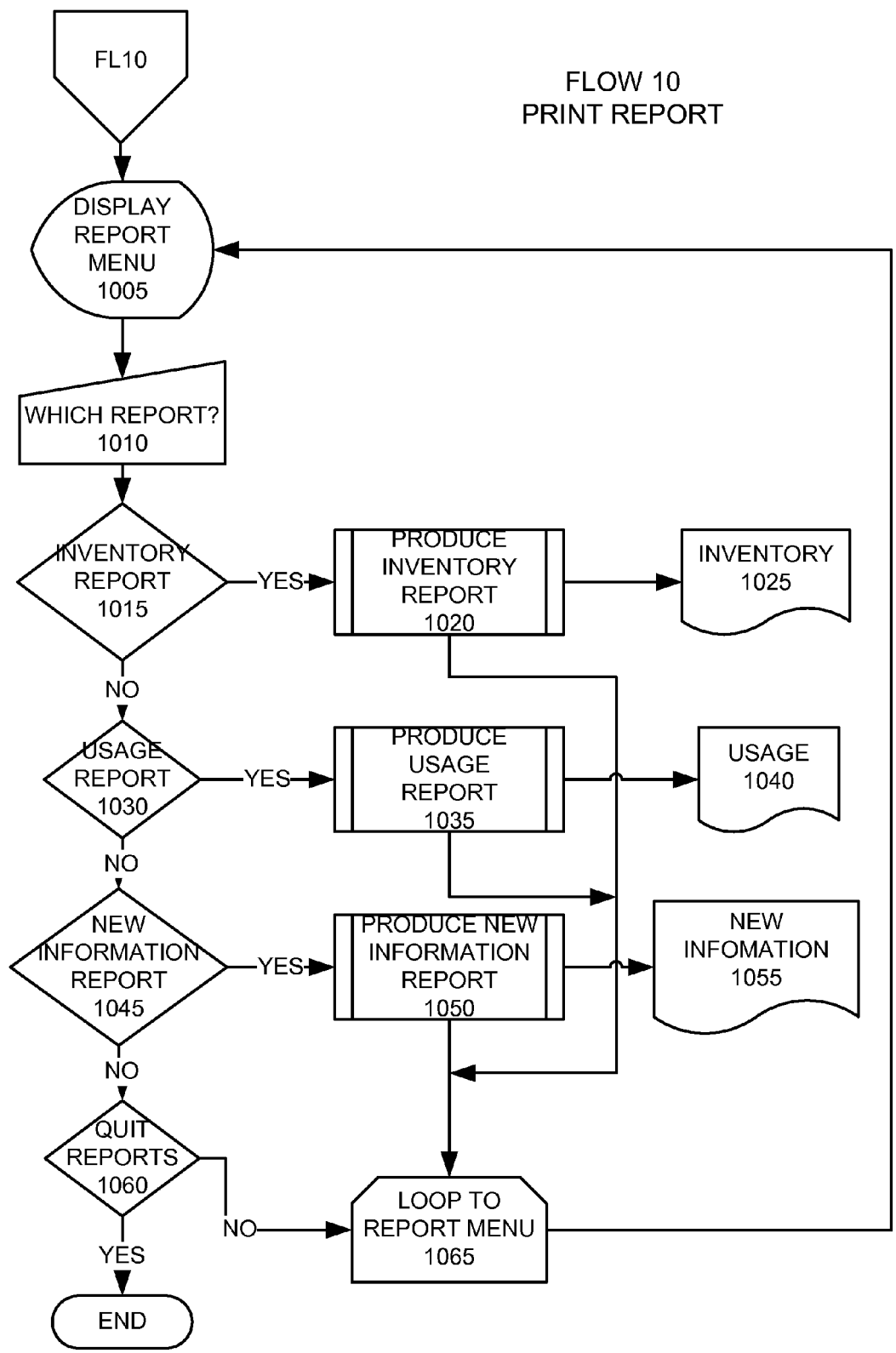

FIG. 10 contains a high-level flow diagram illustrating the steps performed by embodiments of the invention when the operator has requested a printed report. As shown in FIG. 10, the system first displays a report menu and prompts the operator to select the report desired (steps 1005 and 1010). If the operator selects an inventory report, the system will produce (and optionally print) an inventory report based on data retrieved from an inventory file or database (steps 1015, 1020 and 1025). If the operator selects a usage report, the system will produce (and optionally print) a usage report based on data retrieved from an optional usage file or database (steps 1030, 1035 and 1040). If the operator elects to receive a report containing any new information about the pharmaceutical product, the system will produce (and optionally print) a report containing the new information based on data retrieved from an optional new information file or database (steps 1045, 1050 and 1055). Preferably, the system is configured to loop through these reporting options until the operator quits out of the report menu (steps 1060 and 1065).

Figure 11:
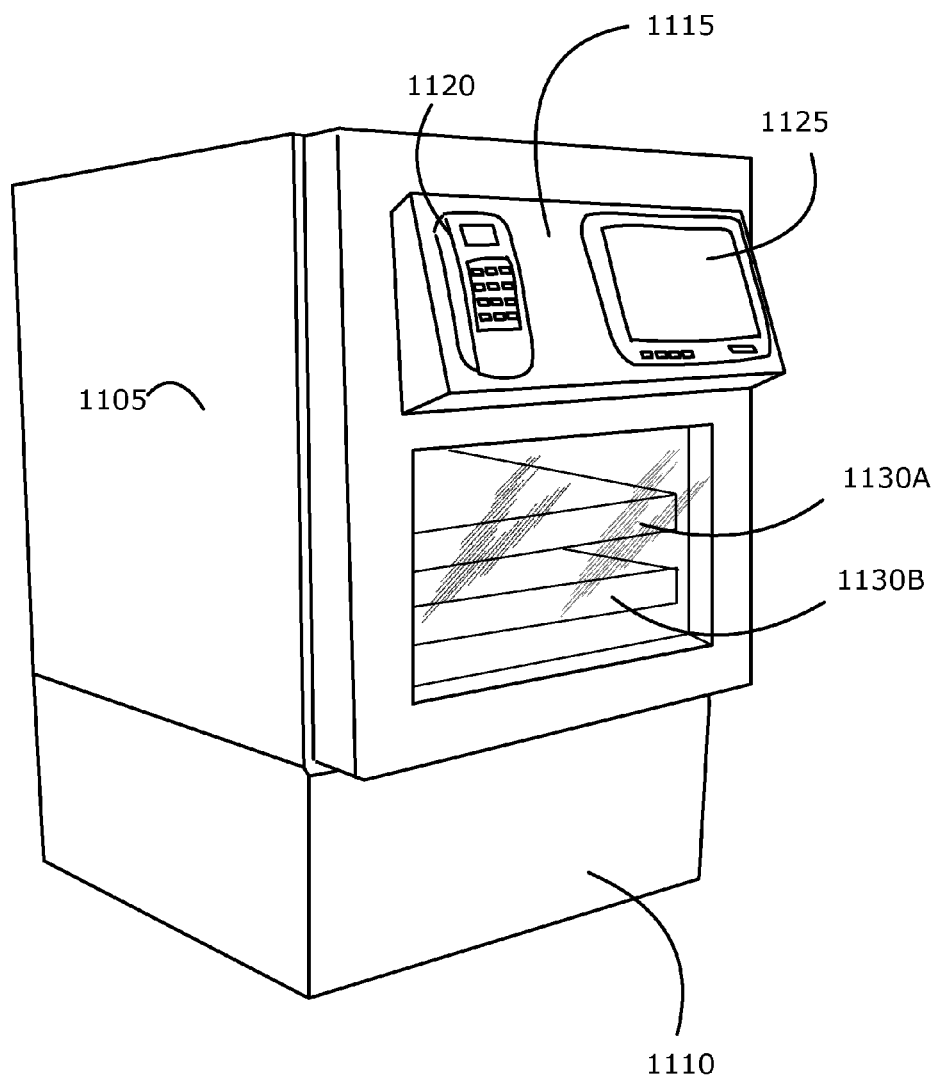
FIG. 11 shows an exterior view of an exemplary embodiment of the invention.

FIG. 11 shows an exterior view of an exemplary embodiment of the invention as it might be viewed from a viewpoint that lies approximately halfway between the front and side perspective views. The embodiment depicted in FIG. 11 illustrates by way of example one possible configuration for the cold storage compartment 1105, processor compartment 1110 and input/output devices 1115, which are discussed in greater detail above and with reference to FIG. 1. In the embodiment shown in FIG. 11, input/output devices 1115 includes a keypad 1120, which may be activated by a human operator to enter security codes and/or operating instructions for the refrigerator, and a touchpad display 1125 configured to display to the human operator error messages, information and warnings associated with pharmaceutical product containers inside the refrigerator, as well as information related to the operational status of the refrigerator itself. Touchpad display 1125 may also be configured to accept menu-based commands and instructions from a human operator. FIG. 11 also illustrates one possible arrangement for the shelves inside the cold storage compartment (shown in FIG. 11 as shelves 1130A and 1130B), upon which the pharmaceutical product containers may be stored. In the exemplary embodiment depicted in FIG. 11, shelves 1130A and 1130B can be seen through a window of transparent or semi-transparent glass or plastic embedded in the door of the unit.

Although the exemplary embodiments, uses and advantages of the invention have been disclosed above with a certain degree of particularity, it will be apparent to those skilled in the art upon consideration of this specification and practice of the invention as disclosed herein that alterations and modifications can be made without departing from the spirit or the scope of the invention, which are intended to be limited only by the following claims and equivalents thereof. It should be recognized by those skilled in the art, for instance, that while one of the embodiments disclosed herein relies on the generation and use of event codes, alternative embodiments of the invention may be implemented without generating and using such event codes, and that such alternative embodiments fall within the scope of the claimed invention.

What is claimed is:

1. A refrigerator, comprising:
 a cold storage compartment configured to hold a plurality of pharmaceutical product containers;
 a local database for storing information associated with the plurality of pharmaceutical product containers located in the cold storage compartment;
 an RFID reader configured to determine a unique identifier for a pharmaceutical product container added to the cold storage compartment based on a radio frequency identification signal produced by the added pharmaceutical product container; and
 a processor configured to determine, based on the information in the local database and the unique identifier, (i) whether the added pharmaceutical product container was previously removed from the cold storage compartment, (ii) a length of time that the added pharmaceutical product container was most recently removed from the cold storage compartment, and (iii) an updated total time out of refrigeration value for the pharmaceutical product container, wherein the processor calculates the updated total time out of refrigeration value by retrieving a prior total time out of refrigeration value from the local database and adding thereto said most recently removed length of time;
 wherein the processor is further configured to modify the information in the local database to include the length of time that the added pharmaceutical product container was most recently removed and the updated total time out of refrigeration value.

2. The refrigerator of claim 1, wherein the processor is further configured to cause a message concerning the added pharmaceutical product container to be delivered to a human operator, the message including at least one of: the unique identifier, the length of time elapsed since the added pharmaceutical product container was previously removed from the cold storage compartment or the updated total length of time that the added pharmaceutical product container has been removed from the cold storage compartment.

3. The refrigerator of claim 1, wherein the processor causes the message to be delivered to the human operator via at least one of: an information store, a log file, an attached output device, an email communication program, a web page server, or an online information publication service.

4. The refrigerator of claim 1, wherein:
 the processor is electronically coupled to a clock configured to provide a current date;
 the information in the local database is includes a record specifying an expiration date for the added pharmaceutical product container; and
 the processor is further configured to (i) determine an expiration status for the added pharmaceutical product container by comparing the current date to the expiration date, and (ii) cause a warning to be delivered to the human operator concerning the expiration status of the pharmaceutical product container.

5. The refrigerator of claim 1, wherein:
 the information in the local database includes a record specifying a maximum time out of refrigeration value for the added pharmaceutical product container; and
 the processor is further configured to (i) determine a spoliation status for the pharmaceutical product container by comparing the updated total length of time to the maximum time out of refrigeration value, and (ii) cause a warning to be delivered to the human operator concerning the spoliation status of the pharmaceutical product container.

6. The refrigerator of claim 1, wherein:
the processor is electronically coupled to a clock configured to provide a current time;
the information in the local database comprises a record for storing (i) a removal time indicating a time that the added pharmaceutical product was previously removed from the cold storage compartment, and (ii) a prior total length of time that the added pharmaceutical product container has been removed from the cold storage compartment; and
the processor determines the updated total length of time that the pharmaceutical product container has been removed from the cold storage compartment by retrieving the current time from the clock, retrieving the removal time and the old total length of time from the local database, subtracting the removal time from the current time to obtain a duration, and adding the duration to the prior total length of time.

7. The refrigerator of claim 1, wherein if the processor determines that the added pharmaceutical product container was not previously removed from the cold storage compartment, then the processor will cause the time that the added pharmaceutical product container was added to the cold storage compartment to be recorded in the local database.

8. The refrigerator of claim 7, further comprising:
an interface to a pharmaceutical product database;
wherein the processor is further configured to (i) determine whether the pharmaceutical product database contains a set of details associated with the unique identifier, and (ii) cause a copy of the set of details to be copied from the pharmaceutical product database to the local database via the interface.

9. The refrigerator of claim 8, wherein if the processor determines that the pharmaceutical product database does not contain a set of details associated with the unique identifier, then the processor will create a record in the local database indicating that the authenticity of the pharmaceutical product container is suspect.

10. The refrigerator of claim 9, wherein the processor is further configured to cause a warning to be delivered to the human operator concerning the suspect authenticity of the pharmaceutical product container.

11. The refrigerator of claim 1, wherein:
the cold storage compartment includes a temperature sensor that measures the temperature in the cold storage compartment; and
the processor periodically compares the temperature in the cold storage compartment to a specified temperature setting and delivers a warning message to the human operator if the temperature in the cold storage compartment differs from the specified temperature setting.

12. A refrigerator for storing pharmaceutical product containers, comprising:
a cold storage compartment configured to hold a plurality of pharmaceutical product containers;
an RFID reader configured to determine a unique identifier for a pharmaceutical product container located inside the cold storage compartment based on a radio frequency identification signal emitted by a transponder affixed to the pharmaceutical product container;
a local database comprising a record correlating the unique identifier with a prior total time out of refrigeration value for the pharmaceutical product container;
a power fail circuit for detecting a power failure condition for the refrigerator; and
a processor, electronically coupled to the RFID reader, the local database and the power fail circuit, that determines a duration for the power fail condition, calculates a new total time out of refrigeration value for the pharmaceutical product container by retrieving the prior total time out of refrigeration value from the local database and adding the duration to the prior total time out of refrigeration value, and stores the new time out of refrigeration value in the local database.

13. The refrigerator of claim 12, wherein the processor is further configured cause a message concerning the power failure condition to be delivered to a human operator via one or more of an information store, a log file, an attached output device, an email communication, a web page server, and an online information publication service.

14. A refrigerator, comprising:
a cold storage compartment configured to hold a plurality of pharmaceutical product containers;
an RFID reader configured to determine a plurality of unique identifiers for the plurality pharmaceutical containers located inside the cold storage compartment based on a respective plurality of radio frequency identification signals produced by the plurality of pharmaceutical product containers;
a local database comprising records correlating the plurality of unique identifiers with a plurality of details associated with the plurality of pharmaceutical product containers located in the cold storage compartment; and
a processor configured to determine, based on the plurality of unique identifiers and the plurality of details in the local database, whether a pharmaceutical product container has been removed from the cold storage compartment;
wherein the processor is configured to (i) record in the local database the time that the pharmaceutical product container was removed from the cold storage compartment, and (ii) cause a message to be delivered to a human operator indicating that the pharmaceutical product container was removed from the cold storage compartment; and
wherein the processor is configured to determine an updated total time out of refrigeration value for the pharmaceutical product container by retrieving a prior total time out of refrigeration value from the local database and adding thereto a length of time that the pharmaceutical product container was most recently removed from the cold storage compartment.

15. The refrigerator of claim 14, wherein the processor is further configured to determine, based on the unique identifier and the plurality of details in the local database, an expiration status for the pharmaceutical product container removed from the cold storage compartment, and cause a message concerning the expiration status to be delivered to the human operator.

16. The refrigerator of claim 14, wherein the processor is further configured to determine, based on the unique identifier and the plurality of details in the local database, a recall status for the pharmaceutical product container removed from the cold storage compartment, and cause a message concerning the recall status to be delivered to the human operator.

17. The refrigerator of claim 14, wherein:
the plurality of details in the local database comprises a record indicating a specified maximum time out of refrigeration value for the pharmaceutical product container; and
the processor is further configured to determine, based on the updated total time out of refrigeration value and said specified maximum time out of refrigeration value, a spoliation status for the pharmaceutical product container removed from the cold storage compartment, and cause a message concerning the spoliation status to be delivered to the human operator.

18. The refrigerator of claim 14, wherein:

the cold storage compartment includes a temperature sensor that measures the temperature in the cold storage compartment; and the processor periodically compares the temperature measured by the temperature sensor to a specified temperature value and, if the temperature differs from the specified temperature value, generates an alert concerning the temperature.

19. A refrigerator for pharmaceutical products, comprising:
 - a cold storage compartment configured to hold a plurality of pharmaceutical product containers configured to produce a plurality of RFID signals, respectively;
 - an RFID reader;
 - a local database;
 - an interface to a pharmaceutical product database; and
 - a processor;
 - wherein the processor is operable with the RFID reader, the local database and the interface to periodically perform the following steps (a) through (e) for each pharmaceutical product container located inside the cold storage compartment,
   - (a) determine a unique identifier for said each pharmaceutical product container based on the RFID signal emitted therefrom,
   - (b) determine if the local database includes a set of details associated with the unique identifier,
   - (c) if the local database does not include the set of details, attempt to copy the set of details from the pharmaceutical product database to the local database via the interface,
   - (d) deliver a warning message to a human operator if the attempt to copy the set of details from the pharmaceutical product database to the local database via the interface is not successful, and
   - (e) determine an updated total time out of refrigeration value for the pharmaceutical product container by retrieving a prior total time out of refrigeration value from the local database and adding thereto a length of time that the pharmaceutical product container was most recently removed from the cold storage compartment.

20. The refrigerator of claim 19, wherein:

the cold storage compartment includes a temperature sensor that measures the temperature in the cold storage compartment; and the processor is further configured to (i) periodically compare the temperature in the cold storage compartment to a specified temperature setting, and (ii) deliver a warning message to a human operator if the temperature in the cold storage compartment differs from the specified temperature setting.

21. The refrigerator of claim 19, wherein:

the set of details associated with each unique identifier includes the updated total time out of refrigeration value and a specified maximum time out of refrigeration value; and the processor is further configured to periodically perform the following steps (f) and (g) for each pharmaceutical product container located inside the cold storage compartment, based on each unique identifier,
 - (f) compare the updated total time out of refrigeration value to the specified maximum time out of refrigeration value, and
 - (g) deliver a warning to a human operator if the updated total time out of refrigeration value exceeds the specified maximum time out of refrigeration value.

22. The refrigerator of claim 21, further comprising:

a power fail circuit for detecting a power failure condition in the refrigerator;

wherein the processor is further configured to periodically determine a duration for the power fail condition, calculate a new total time out of refrigeration value for each pharmaceutical product container in the cold storage compartment by adding the duration to the total time out of refrigeration value for said each pharmaceutical product container, and store the new total time out of refrigeration value for said each pharmaceutical product container in the local database.

\* \* \* \* \*